United States Patent
Przewosny et al.

(10) Patent No.: US 6,642,267 B2
(45) Date of Patent: Nov. 4, 2003

(54) SUBSTITUTED 1,5-DIHYDROPYRROL-2-ONE DERIVATIVES ACTIVE AS NMDA RECEPTOR ANTAGONISTS FOR TREATMENT OF STATES OF PAIN

(75) Inventors: Michael Przewosny, Aachen (DE); Hans-Dietrich Stachel, Neuried (DE); Hermann Poschen-Rieder, Graefelfing (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/066,800

(22) Filed: Feb. 6, 2002

(65) Prior Publication Data
US 2002/0161033 A1 Oct. 31, 2002

Related U.S. Application Data

(63) Continuation of application No. PCT/EP00/07100, filed on Jul. 25, 2000.

(30) Foreign Application Priority Data
Aug. 6, 1999 (DE) .......................... 199 36 719

(51) Int. Cl.[7] ........................ A61K 31/40; C07D 207/44
(52) U.S. Cl. ........................ 514/425; 548/542; 548/544; 548/546; 548/550
(58) Field of Search ........................ 548/550, 546, 548/542, 544; 514/425

(56) References Cited

FOREIGN PATENT DOCUMENTS

DE 1236510 * 3/1967

* cited by examiner

*Primary Examiner*—Joseph K. McKane
*Assistant Examiner*—Kamal Saeed
(74) *Attorney, Agent, or Firm*—Crowell & Moring LLP

(57) ABSTRACT

A substituted 1,5-dihydropyrrol-2-one compound of formula I:

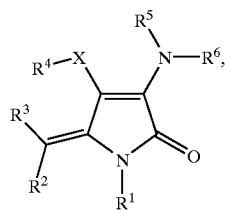

and methods for preparing the compounds. Also disclosed are pharmarceutical compositions comprising the compounds and methods of using the compounds for the treatment or prophylaxis of pain, inflammatory and allergic reactions, depressions, drug abuse and various other diseases or conditions.

45 Claims, No Drawings

SUBSTITUTED 1,5-DIHYDROPYRROL-2-ONE DERIVATIVES ACTIVE AS NMDA RECEPTOR ANTAGONISTS FOR TREATMENT OF STATES OF PAIN

CROSS REFERENCE TO RELATED APPLICATIONS

The present application is a continuation of international patent application no. PCT/EP00/07100, filed Jul. 25, 2000, designating the United States of America, the entire disclosure of which is incorporated herein by reference. Priority is claimed based on Federal Republic of Germany patent application no. DE 199 36 719.1, filed Aug. 6, 1999.

BACKGROUND AND SUMMARY OF THE INVENTION

The invention relates to substituted 1,5-dihydropyrrol-2-one derivatives, processes for their preparation, medicaments comprising these compounds, and the use of these compounds for the preparation of medicaments.

The treatment of chronic and non-chronic states of pain is of great importance in medicine. There is a worldwide demand for pain treatments which have a good efficacy. The urgent need for action in respect of patient-relevant and target-orientated treatment of chronic and non-chronic states of pain, this being understood as meaning successful and satisfactory pain treatment for the patient, is documented in the large number of scientific works which have recently appeared in the field of applied analgesia and fundamental research into nociception.

Conventional opioids, such as e.g. morphine, have a good action in the treatment of severe to very severe pain. However, their use is limited due to the known side effects, e.g. respiratory depression, vomiting, sedation, constipation, addiction, dependency and development of tolerance. They can therefore be administered over a relatively long period of time or in relatively high dosages only with particular safety precautions, such as e.g. specific prescription instructions (Goodman, Gilman, The Pharmacological Basis of Therapeutics, Pergamon Press, New York 1990). Furthermore, they have a relatively low efficacy for some states of pain, in particular neuropathic and incidental pain.

Opioids display their analgesic action by bonding to receptors on the membrane which belong to the family of so-called G protein-coupled receptors. In addition, there are further receptors and ion channels which are considerably involved in the system of pain formation and pain conduction, such as e.g. the N-methyl-D-aspartate (NMDA) ion channel, via which a considerable part of the communication of synapses proceeds and through which the calcium ion exchange between a neuronal cell and its environment is controlled.

Knowledge of the physiological importance of ion channel-selective substances has been acquired by the development of the patch clamp technique, with which the action of NMDA antagonists on the calcium balance inside the cell can be demonstrated.

An object on which the invention is based was to provide new compounds which are suitable for pain treatment or for anxiolysis. Furthermore, these compounds should have as few as possible of the side effects of opioid analgesics, such as e.g. nausea, vomiting, dependency, respiratory depression or constipation. Further objects were to provide new active compounds for treatment of inflammatory and/or allergic reactions, depressions, drug and/or alcohol abuse, gastritis, diarrhoea, urinary incontinence, cardiovascular diseases, respiratory tract diseases, coughing, mental illnesses, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome, tinnitus aurium or perinatal asphyxia.

DETAILED DESCRIPTION OF THE INVENTION

It has now been found that substituted 1,5-dihydropyrrol-2-one derivatives of the following general formula I, as NMDA antagonists, selectively attack the glycine bonding site and are suitable for treatment of inflammatory and/or allergic reactions, depressions, drug and/or alcohol abuse, gastritis, diarrhoea, urinary incontinence, cardiovascular diseases, respiratory tract diseases, coughing, mental illnesses, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome, tinnitus aurium or perinatal asphyxia. The compounds and derivatives of formula I moreover have a pronounced analgesic and/or anxiolytic action.

The present invention therefore provides substituted 1,5-dihydropyrrol-2-one derivatives of the general formula I:

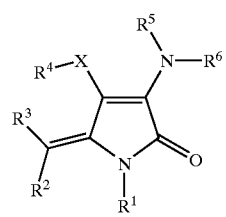

wherein
X represents O, S or $NR^7$;
the radical $R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;
the radicals $R^2$, $R^3$, which are identical or different, represent H, F, Cl, Br, $CF_3$, $OR^{11}$, $SR^{11}$, $NR^9NR^{10}$, a $C_{1-10}$-alkyl, preferably a $C_{1-6}$-alkyl, an aryl or a heteroaryl radical or represent an aryl radical bonded via a $C_{1-6}$-alkylene group, preferably an aryl radical bonded via a $C_{1-3}$-alkylene group;
the radical $R^4$ represents H, OH, $OR^{11}$, $SR^{11}$, $COR^8$, $COOR^8$, $COCOR^8$, $CONR^9R^{10}$, $CSNR^9R^{10}$, a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;
the radicals $R^5$, $R^6$, which are identical or different, represent H, O, OH, $OR^{11}$, $SR^{11}$, $COR^8$, $CSR^8$, $COOR^8$, $COCOR^8$, $CONR^9R^{10}$, $CSNR^9R^{10}$, a $C_{1-10}$-alkyl, preferably a $C_{1-6}$-alkyl, an aryl or a heteroaryl radical, or represent an aryl radical bonded via $C_{1-6}$-alkylene group, preferably an aryl radical bonded via a $C_{1-3}$-alkylene group or $R^5$ and $R^6$ together denote the group =O;
the radical $R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, preferably a $C_{1-6}$-alkyl, an aryl or a heteroaryl radical or represents an aryl radical bonded via a $C_{1-6}$-alkylene group, preferably an aryl radical bonded via a $C_{1-3}$-alkylene group;

the radical $R^8$ represents H, $OR^{11}$, $SR^{11}$, $NR^9R^{10}$, a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;

the radical $R^9$ represents a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;

the radical $R^{10}$ represents a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;

the radical $R^{11}$ represents a $C_{1-10}$-alkyl, preferably a $C_{1-6}$-alkyl, an aryl or a heteroaryl radical, or represents an aryl radical bonded via a $C_{1-6}$-alkylene group, preferably an aryl radical bonded via a $C_{1-3}$-alkylene group;

in the form of their racemates, enantiomers, diastereomers or a corresponding base or a corresponding physiologically tolerated salt, with the proviso that the racemates of 1-methyl-3-acetamino-5-ethoxymethylenetetramic acid, of 3-acetamino-5-ethoxymethylenetetramic acid, of α-acetylamino-γ-benzylthiomethylenetetramic acid of the acetamide of N-[2,5-dihydro-2-oxo-4-[(phenylmethyl)thio]-5-[[(phenylmethyl)thio]methylene]-1H-pyrrol-3-yl], of the acetamide of N-[2,5-dihydro-2-oxo-1-(phenylmethyl)-4-[(phenylmethyl)thio]-5-[[(phenylmethyl)thio]methylene]-1H-pyrrol-3-yl], of the benzamide of N-[2,5-dihydro-2-oxo-1-(phenylmethyl)-4-[(phenylmethyl)thio]-5-[[(phenylmethyl)thio]methylene]-1-H-pyrrol-3-yl], of the acetamide of N-[2,5-dihydro-1-methyl-2-oxo-4-[(phenylmethyl)thio]-5-[[(phenylmethyl)thio]methylene]-1H-pyrrol-3-yl], of the propanamide of N-[2,5-dihydro-1-methyl-2-oxo-4-[(phenylmethyl)thio]-5[[(phenylmethyl)thio]methylene]-1H-pyrrol-3-yl], and the geometric isomers of the acetamide of N-[2,5-dihydro-1-methyl-2-oxo-4-[(phenylmethyl)thio]-5-[[(phenylmethyl)thio]methylene]-1H-pyrrol-3-yl]-, (E)-, of the acetamide of N-[2,5-dihydro-1-methyl-2-oxo-4-[(phenylmethyl)thio]-5-[[(phenylmethyl)thio]methylene]-1H-pyrrol-3-yl]-, (Z)-, of the propanamide of N-[2,5-dihydro-1-methyl-2-oxo-4-[(phenylmethyl)thio]-5-[[(phenylmethyl)thio]methylene]-1H-pyrrol-3-yl]-, (E)-, and of the propanamide of N-[2,5-dihydro-1-methyl-2-oxo-4-[(phenylmethyl)thio]-5-[[(phenylmethyl)thio]methylene]-1H-pyrrol-3-yl]-, (Z)-are excluded.

As used in the instant specification, alkyl radicals are understood as meaning branched, unbranched or cyclic hydrocarbons which are unsubstituted or at least monosubstituted, preferably by F, Cl, Br, CN, $NO_2$, CHO, $SO_2C_{1-6}$-alkyl, $SO_2CF_3$, $OR^8$, $NR^9R^{10}$, $COR^8$, $COOR^8$, $COCOR^8$, $CONR^9R^{10}$ and/or $CSNR^9R^{10}$, where the radicals $R^8$ to $R^{10}$ have the meaning according to the general formula I as defined above. If the alkyl redicals contain more than one substituent, these can be identical or different. The alkyl radicals are preferably methyl, ethyl, propyl, isopropyl, n-butyl, sec-butyl, tert-butyl, neopentyl, n-hexyl, cyclopropyl, cyclobutyl, cyclopentyl or cyclohexyl.

An aryl radical is understood as meaning phenyls which are unsubstituted or at least monosubstituted by OH, F, Cl, Br, $CF_3$, CN, $NO_2$, CHO, $SO_2C_{1-6}$-alkyl, $SO_2CF_3$, $NR^9R^{10}$, $COR^8$, $COOR^8$, $COCOR^8$, $CONR^9R^{10}$, $CSNR^9R^{10}$, a $C_{1-6}$-alkyl radical, a $C_{1-6}$-alkoxy radical, a $C_{2-6}$-alkylene radical, a heterocyclyl radical and/or a phenyl radical, wherein the radicals $R^8$ to $R^{10}$ have the meaning according to the general formula I. If the aryl radicals contain more than one substituent, these can be identical or different. The term can also denote naphthyl. The phenyl radicals can also be fused with further rings.

A heteroaryl radical is understood as meaning 5- or 6-membered unsaturated heterocyclic compounds which are optionally provided with a fused-on aryl radical and contain at least one heteroatom, preferably nitrogen, oxygen and/or sulfur. The heteroaryl radical is preferably furan, thiophene, pyrrole, pyridine, pyrimidine, quinoline, isoquinoline, phthalazine or quinazoline.

The following substituted 1,5-dihydropyrrol-2-one derivatives are particularly preferred:

5-benzylidene-4-methoxy-3-nitroso-1,5-dihydropyrrol-2-one 4-benzylamine-5-benzylidene-3-nitroso-1,5-dihydropyrrol-2-one 5-benzylidene-4-hydroxy-3-nitroso-1,5-dihydro-pyrrol-2-one.

5-benzylidene-3-nitroso-4-phenylamino-1,5-dihydropyrrol-2-one, 5-benzylidene-4-methylamino-3-nitroso-1,5-dihydropyrrol-2-one, 4-amino-5-benzylidene-3-nitroso-1,5-dihydropyrrol-2-one, 5-benzylidene-4-hydroxy-3-nitro-1,5-dihydropyrrol-2-one, 5-benzylidene-3-nitro-4-phenylamino-1,5-dihydropyrrol-2-one, 4-benzylamino-5-benzylidene-3-nitro-1,5-dihydropyrrol-2-one, 5-benzylidene-4-methylamino-3-nitro-1,5-dihydropyrrol-2-one and 4-amino-5-benzylidene-3-nitro-1,5-dihydropyrrol-2-one.

The invention also provides processes for the preparation of substituted 1,5-dihydropyrrol-2-one derivatives of the general formula I. According to the instant invention, tetram acids of the general formula II:

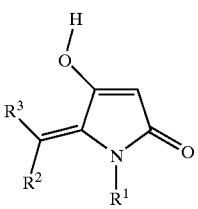

II wherein the radicals $R^1$ to $R^3$ have the meaning according to the general formula I, are reacted with an aqueous solution of alkali metal nitrite, preferably sodium nitrite, at a low temperature in solution, preferably in an ice-cooled acid solution, particularly preferably in an ice-cooled acid solution of glacial acetic acid, to give rise to compounds of the general formula III:

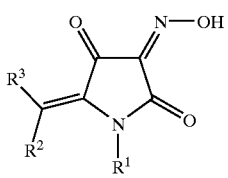

III wherein the radicals $R^1$ to $R^3$ have the meaning according to the general formula I. The compounds of formula III are preferably purified by recrystallization, preferably from ethanol, and isolated. These compounds of the general formula III are in general present as a mixture with the corresponding nitroso tautomers.

The synthesis of the starting compounds, the tetramic acids of the general formula II, can be carried out in accordance with H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696) and the literature references cited therein, all of which are incorporated herein by reference.

The compounds of the general formula III wherein $R^1$ to $R^3$ have the meaning according to the general formula I can be converted by alkylation with alkylating agents known per se, preferably with diazoalkanes, dialkyl sulfates or alkyl halides in solution, particularly preferably with diazoalkanes in ethereal solution, or by reaction with acid chlorides, acid bromides, chlorocarbonic acid esters, fluorocarbonic acid esters, isocyanates and/or isothiocyanates in non-polar solvents, preferably in open-chain or cyclic ethers, hydrocarbons, halogen-containing hydrocarbons and/or in polar, aprotic solvents, preferably in dimethylformamide and/or N-methylpyrrolidone and/or in polar, protic solvents, preferably dimethylsulfoxide, into compounds of the general formula IV:

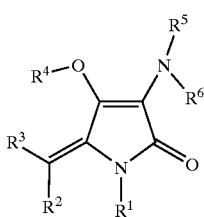

IV wherein the radicals $R^1$ to $R^4$ have the meaning according to the general formula I and the radicals $R^5$ and $R^6$ together denote the group $=O$, which are purified and isolated by conventional methods.

The compounds of the general formula IV wherein the radicals $R^1$ to $R^4$ have the meaning according to the general formula I and the radicals $R^5$ and $R^6$ together denote the group $=O$ can be derivatized still further in that they are reacted with nucleophiles, preferably with primary or secondary amines, aliphatic, aromatic or heteroaromatic alcoholates or corresponding thiolates, phenolates and/or thiophenolates, in polar solvents, preferably in methanol, ethanol and/or isopropanol, to give compounds of the general formula V:

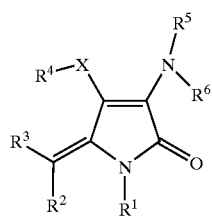

V wherein the radicals $R^1$ to $R^4$ and X have the meaning according to the general formula I and the radicals $R^5$ and $R^6$ together denote the group $=O$, are purified by recrystallization, preferably by recrystallization from methanol, ethanol and/or isopropanol, and isolated.

The compounds of the general formula V wherein the radicals $R^1$ to $R^4$ and X have the meaning according to the general formula I and the radicals $R^5$ and $R^6$ together denote the group $=O$, can be reduced to compounds of the general formula I wherein the radicals $R^5$ and $R^6$ each denote H and $R^1$ to $R^4$ and X have the meaning according to the general formula I by reaction with a reducing agent, preferably with Zn/glacial acetic acid, lithium aluminium hydride, $BH_3$, $Na[BH_3CN]/TiCl_3$, sodium alkoxides or by hydrogenation with hydrogen in the presence of transition metal catalysts.

A further derivatization of the compounds of the general formula I in which $R^5$ and $R^6$ each denote H and $R^1$ to $R^4$ and X have the meaning according to the general formula I to give compounds of the general formula I wherein the radicals $R^5$, $R^6$, which are identical or different, represent O, OH, $OR^{11}$, $SR^{11}$, $COR^8$, $CSR^8$, $COOR^8$, $COCOR^8$, $CONR^9R^{10}$, $CSNR^9R^{10}$ a $C_{1-10}$-alkyl radical, an aryl radical, a heteroaryl radical or represent an aryl radical bonded via a $C_{1-6}$-alkylene group and the radicals $R^1$ to $R^4$ and X have the meaning according to the general formula I can be carried out by various methods known to those skilled in the art.

The compounds of the general formula V wherein $R^5$ and $R^6$ together denote the group $=O$ can also be obtained by oxidation of the compounds of the general formula III, preferably with $KMnO_4$ and peroxytrifluoroacetic acid, and are purified and isolated by conventional processes.

The compounds of the general formula I according to the invention can be converted with acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid, into the corresponding physiologically tolerated salts in a manner well known to an ordinarily skilled person in the art. The salt formation is preferably carried out in a solvent, such as diethyl ether, diisopropyl ether, acetic acid alkyl esters, acetone and/or 2-butanone.

Trimethylchlorosilane in aqueous solution is moreover suitable for preparation of the corresponding hydrochlorides.

The substituted 1,5-dihydropyrrol-2-one derivatives of the general formula I according to the invention are toxicologically acceptable and therefore represent suitable pharmaceutical active compounds.

The invention therefore also provides medicaments or pharmaceutical compositions which comprise, as the active compound, at least one substituted 1,5-dihydropyrrol-2-one derivative of the general formula I and/or a corresponding base and/or a corresponding physiologically tolerated salt and optionally further active compounds and auxiliary substances such as pharmaceutically acceptable excipients. The medicament can also comprise a mixture of at least two enantiomers and/or corresponding bases and/or corresponding physiologically tolerated salts of a compound of the general formula I according to the invention, the enantiomers not being present in equimolar mixtures.

The medicaments are preferably employed for control of pain or for treatment of inflammatory and/or allergic reactions, depressions, drug and/or alcohol abuse, gastritis, diarrhoea, urinary incontinence, cardiovascular diseases, respiratory tract diseases, coughing, mental illnesses, neurodegenerative diseases, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, deficiency states of the central nervous system, hypoxia, anoxia, AIDS dementia, encephalomyelitis, Tourette's syndrome, perinatal asphyxia, tinnitus aurium or for anxiolysis.

The invention also provides methods for using at least one substituted 1,5-dihydropyrrol-2-one derivative of the general formula I and/or a corresponding base and/or a corresponding physiologically tolerated salt for the preparation of a medicament for control of pain and/or for treatment of inflammatory and/or allergic reactions, depressions, drug and/or alcohol abuse, gastritis, diarrhoea, urinary incontinence, cardiovascular diseases, respiratory tract diseases, coughing, mental illnesses, neurodegenerative diseases, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, deficiency states of the central nervous system, hypoxia, anoxia, AIDS dementia, encephalomyelitis, Tourette's syndrome, perinatal asphyxia, tinnitus aurium or for anxiolysis.

To prepare corresponding pharmaceutical formulations, in addition to at least one substituted 1,5-dihydropyrrol-2-one derivative of the general formula I, auxiliary substances, or excipients, such as carrier materials, fillers, solvents, diluents, dyestuffs and/or binders can be employed. The choice of auxiliary substances and the amounts thereof to be employed are well-known to one skilled in the art and depend on whether the medicament is to be administered orally, intravenously, intraperitoneally, intradermally, intramuscularly, intranasally, buccally or locally, for example on infections on the skin, the mucous membranes and on the eyes. Formulations in the form of tablets, coated tablets, capsules, drops, juices and syrups as well as multiparticulate formulations, for example pellets or granules, which can optionally also be filled in capsules or pressed to tablets, are suitable for oral administration, and solutions, suspensions, easily reconstitutable dry formulations and sprays are suitable for parenteral, topical and inhalatory administration. Compounds of the general formula I according to the invention in a depot, in dissolved form or in a patch, optionally with the addition of agents which promote penetration of the skin, are suitable percutaneous administration formulations. Formulation forms which can be used orally or percutaneously can release the compounds of the general formula I according to the invention in a retarded manner.

The amount of active compound to be administered to the patient varies according to the weight of the patient, the mode of administration, the indication and the severity of the illness. Two to 500 mg/kg of at least one substituted 1,5-dihydropyrrol-2-one derivative of the general formula I are usually administered.

Pharmacological studies:

a) Receptor binding studies

The studies for determination of the affinity of the substituted 1,5-dihydropyrrol-2-one derivatives of the general formula I for the glycine-binding site of the NMDA receptor channel were carried out on brain membrane homogenates (homogenate of the cortex and hippocampus area from the brain of male rats, Wistar strain, Charles River, WIGA GmbH, Sulzbach, Germany) by the method of Baron B. M. et al, J. Pharmacol. Exp. Ter., vol. 279, pp. 62–68 (1996).

Specifically, the cortex and hippocampus were exposed from freshly removed rat brains and homogenized in 5 mmol/l TRIS-acetate buffer, 0.32 mol/l sucrose pH 7.4 (10 ml/g fresh weight) with a Potter homogenizer (Braun, Melsungen, Germany, 10 plunger strokes at 500 revolutions per minute (rpm)), while cooling with ice, and the mixture was then centrifuged for 10 minutes at 1,000 g and 4° C. The first supernatant was collected and the sediment was homogenized again with 5 mmol/l TRIS-acetate buffer, 0.32 mol/l sucrose pH 7.4 (5 ml/g of original fresh weight of rat brain cortex and hippocampus) with the Potter homogenizer (10 plunger strokes at 500 rpm), while cooling with ice, and the mixture was centrifuged for 10 minutes at 1,000 g and 4° C. The resulting supernatant was combined with the supernatant from the first centrifugation and the mixture was centrifuged at 17,000 g for 20 minutes at 4° C. The supernatant after this centrifugation was discarded and the membrane sediment was taken up in 5 mmol/l TRIS-acetate buffer pH 8.0 (20 ml/g original fresh weight) and the mixture was homogenized with 10 plunger strokes at 500 rpm.

The membrane homogenate was then incubated for 1 hour at 4° C. and centrifuged for 30 minutes at 50,000 g and 4° C. The supernatant was discarded and the centrifuge tube with the membrane sediment was closed with Parafilm and frozen for 24 hours at −20° C. On the following day the membrane sediment was thawed and taken up in ice-cold 5 mmol/l TRIS-acetate buffer, 0.1% saponin (weight/volume) pH 7.0 (10 ml/g original fresh weight) and the mixture was homogenized with 10 plunger strokes at 500 rpm and then centrifuged for 20 minutes at 50,000 g and 4° C. The resulting supernatant was discarded and the sediment was taken up in a small volume of 5 mmol/l TRIS-acetate buffer pH 7.0 (approx. 2 ml/g original fresh weight) and the mixture was homogenized again with 10 plunger strokes at 500 rpm. After the protein content had been determined, the membrane homogenate was adjusted to a protein concentration of 10 mg protein/ml with 5 mmol/l TRIS-acetate buffer pH 7.0 and frozen in aliquots until the analysis was carried out.

For the receptor binding test, aliquots were thawed, diluted 1:10 with 5 mmol/l TRIS-acetate buffer pH 7.0 and homogenized with the Potter homogenizer with 10 plunger strokes at 500 rpm, while cooling with ice, and the mixture was centrifuged for 60 minutes at 55,000 g at 4° C. The supernatant was decanted and the membrane sediment was adjusted to a protein concentration of 1 mg/ml with ice-cold 50 mmol/l TRIS-acetate buffer pH 7.0 and the mixture was homogenized again with 10 plunger strokes at 500 rpm and kept in suspension while stirring on a magnetic stirrer in an ice-bath. In each case 100 µl of this membrane homogenate per 1 ml batch were employed in the receptor binding test (0.1 mg protein/ml in the final batch).

In the binding test, 50 mmol/l TRIS-acetate buffer pH 7.0 were employed as the buffer and 1 mmol/l ($^3$H)-MDL 105.519 (Baron B. M. at al, J. Pharmacol. Exp. Ther., vol 279, pp. 62–68 (1996)) was employed as the radioactive ligand. The content of non-specific binding was determined in the presence of 1 mmol/l glycine.

In further batches, the compounds according to the invention were added in concentration series and the displacement of the radioactive ligand from its specific binding to the glycine binding site of the NMDA receptor channel was determined. The particular triplicate batches were incubated over 120 minutes at 4° C. and then harvested by means of filtration through glass fibre filter mats (type Whatman GF/B, Adi Hassel, Munich, Germany) for determination of the radioactive ligand bound to the membrane homogenate. The radioactivity retained on the glass fibre filters was measured, after addition of scintillator (Ready Protein, Beckmann Coulter GmbH, Krefeld, Germany), in a β-counter (Packard TRI-CARB Liquid Scintillation Analyzer 2000CA, Packard Instrument, Meriden, Conn. 06450, USA).

The affinity of the compounds according to the invention for the glycine-binding site of the NMDA receptor channel was calculated as the $IC_{50}$ (concentration with 50% displacement of the radioactive ligand from its specific binding) in accordance with the law of mass action by means of non-linear regression and stated as the Ki value after conversion (by the Cheng-Prussof equation (Y. Cheng, W. H. Prusoff, 1973, Biochem. Pharmacol., vol. 22, pp. 3099–3108).

b) NMDA/glycine-induced ion currents in RNA-injected Xenopus oocytes

The study for determination of function changes in the NMDA receptor channel by the compounds of the general formula I according to the invention was carried out on oocytes of the South African clawed toad, *Xenopus laevis*. For this, neuronal NMDA receptor channels were formed in oocytes after injection of RNA from mouse brains and ion currents triggered by co-application of NMDA and glycine were measured.

*Xenopus oocytes* of stages V and VI (Dumont, J. N., J. Morphol., vol. 136, pp. 153–180 (1972)) were micro-injected (100–130 ng/cell) with whole RNA from the brain tissue of adult mice and kept for up to 10 days in culture medium (composition: 88.0 mmol/l NaCl, 1.0 mmol/l KCl, 1.5 mmol/l $CaCl_2$, 0.8 mmol/l $MgSO_4$, 2,4 mmol/l $NaHCO_3$, 5 mmol/l HEPES, 100 IU/ml penicillin, 100 μg/ml streptomycin, pH 7.4) at 20° C. Transmembrane ion currents were recorded with the aid of the conventional two-electrode voltage clamp technique at a holding potential of −70 mV (Bloms-Funke P. et al, (1996) Neurosci. Lett. 205, pp. 115–118 (1996)). The OTC interface and Cellworks software (npi, Federal Republic of Germany) were used to record data and control the test apparatus. The compounds according to the invention were added to a nominally $Mg^{2+}$-free medium (composition: 89.0 mmol/l NaCl, 1.0 mmol/l KCl, 1.8 mmol/l $CaCl_2$, 2.4 mmol/l $NaHCO_3$, 5 mmol/l HEPES, pH 7.4) and applied systemically with the aid of a concentration clamp (npi, Federal Republic of Germany). To test substance effects mediated via the glycine B-binding site of the NMDA receptor channel, the glycine dose/effect curve with and without the particular compound according to the invention was plotted. For this, NMDA in a fixed concentration of 100 μmol/l was co-applied cumulatively with glycine in increasing concentrations (0–100 μmol/l). Thereafter, the experiment was repeated in the same manner with a fixed concentration of the compound according to the invention. The current amplitudes were standardized to those of the control response to co-application of NMDA (100 μmol/l) with glycine (10 μmol/l). The data were analysed with Igor-Pro software (version 3.1, WaveMetrics, USA). All the results were stated as the mean of at least 3 experiments on different oocytes from at least two toads.

The significance for non-paired measurement parameters is determined with the aid of the Mann-Whitney U test and that for paired measurement parameters is determined by the Wilcoxon test (Sysstat, SPSS Inc., USA). $EC_{50}$ values are calculated according to the following formula:

$$Y = Y_{min} + (Y_{max} - Y_{min})/(1 + (X/EC_{50})^{-P})$$

($Y_{min}$=minimum test value, $Y_{max}$=maximum test value, Y=relative current amplitude, X=concentration of the test substance, p=slope factor). In the event of a right-hand shift in the glycine dose/effect curve, the $pA_2$ value of the compound according to the invention was determined graphically with the aid of a Schild regression. Concentration ratios were calculated with the aid of the $EC_{50}$ values, which were calculated independently for each dose/effect curve.

c) Formalin test in mice

The studies for determination of the antinociceptive action of substituted 1,5-dihydropyrrol-2-one derivatives according to the invention were carried out in the formalin test in male albino mice (NMRI, 25–35 g, Iffa Credo, Belgium).

In the formalin test, a distinction is made between the first (early) phase (0–15 min after formalin injection) and the second (late) phase (15–60 min after formalin injection) (D. Dubuisson et al, Pain 4, 161-174 (1977)). The early phase represents a model for acute pain, as a direct reaction to the formalin injection, while the late phase is regarded as a model for persistent (chronic) pain (T. J. Coderre et al, Pain, vol. 52, pp. 259–285 (1993).

The compounds according to the invention were investigated in the second phase of the formalin test to obtain information on substance actions on chronic/inflammatory pain.

By a single subcutaneous formalin injection (20 μl, 1% aqueous solution) into the dorsal side of the right hind paw of freely mobile test animals, a nociceptive reaction was induced, which manifests itself in significant licking and biting of the paw affected.

For the investigation period in the second (late) phase of the formalin test, the nociceptive behaviour was recorded continuously by observing the animals. The pain properties were quantified by adding up the seconds in which the animals showed licking and biting of the paw affected in the investigation period. After injection of substances which have an antinociceptive action in the formalin test, the modes of behaviour described for the animals are reduced, and possibly even eliminated.

In a manner corresponding to the substance tests, in which the animals received an injection of the test substance before formalin, the vehicle, i.e. solvent (e.g. 0.9% NaCl solution), was injected into the control animals before the administration of formalin. The behaviour of the animals after administration of the substance (10 mice per substance dosage) was compared with a control group (10 mice).

On the basis of the quantification of the pain properties, the action of the substance in the formalin test was determined as a change from the control in per cent. The $ED_{50}$ calculations were made by means of regression analysis. The administration time before the formalin injection was chosen according to the mode of administration of the compounds according to the invention (intraperitoneal: 15 min, intravenous: 5 min).

The invention is explained in the following with the aid of examples, but these do not limit the general inventive idea.

EXAMPLES

The yields of the compounds prepared are not optimized. The melting points are uncorrected.

Example 1
5-Benzylidene-4-hydroxy-3-nitroso-1,5-dihydro-pyrrol-2-one

An aqueous solution of sodium nitrite (0.075 g, 1.1 mmol) was added to an ice-cooled suspension of 2 mmol (0.432 g) 5-benzylidene-4-hydroxy-1,5-dihydro-pyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in 5 ml glacial acetic acid, while stirring, and the mixture was stirred at room temperature for 30 minutes. The reaction solution was concentrated and orange crystals of 5-benzylidene-4-hydroxy-4-nitroso-1,5-dihydro-pyrrol-2-one were obtained in a yield of 65% by recrystallization from ethanol. The substance decomposes at 205° C.

Analysis of this compound by means of $^1$H-NMR spectroscopy gave the following signals:
$^1$H-NMR (d6-DMSO, δ in ppm): 14.66 (s, 1 H); 11.25 (s, 0.66 H); 11.18 (s, 0.33 H); 7.64–7.31 (m, 5 H); 6.42 (s, 0.33 H); 6.36 (s, 0.66 H).

Example 2
5-Benzylidene-4-methoxy-3-nitroso-1,5-dihydropyrrol-2-one

An excess of an ethereal diazomethane solution was added to a suspension of 5-benzylidene-4-hydroxy-3-nitroso-1,5-dihydro-pyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in methanol. After the vigorous evolution of nitrogen has subsided, the reaction solution is concentrated in vacuo and the residue thus obtained is recrystallized from methanol. Red crystals of 5-benzylidene-4-methoxy-3-nitroso-1,5-dihydropyrrol-2-one with a melting point of 172° C. were obtained in a yield of 90%.

Analysis of this compound by means of $^1$H-NMR spectroscopy gave the following signals:
$^1$H-NMR (d6-DMSO, δ in ppm): 11.16 (s, 1H); 7.66–7.33 (m, 5H); 6.42 (s, 1H); 4.34 (s, 3H).

Example 3
4-Benzylamino-5-benzylidene-3-nitroso-1,5-dihydropyrrol-2-one

A solution of 0.11 g (0.5 mmol) 5-benzylidene-4-methoxy-3-nitroso-1,5-dihydropyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in methanol was boiled under reflux with 0.25 ml (0.25 mmol) benzylamine for two minutes. The compound 4-benzylamino-5-benzylidene-3-nitroso-1,5-dihydropyrrol-2-one was obtained as red-violet crystals in a yield of 60% after recrystallization from methanol. The compound decomposes at 220° C.

Analysis of this compound by means of $^1$H-NMR spectroscopy gave the following signals:
$^1$H-NMR (d6-DMSO, δ in ppm): 10.06 (s, 1H); 8.09 (s, 1H); 7.57–7.23 (m, 10H); 6.09 (s, 1H); 4.06 (s, 2H).

Example 4
5-Benzylidene-3-nitroso-4-phenylamino-1,5-dihydropyrrol-2-one

A solution of 0.11 g (0.5 mmol) 5-benzylidene-4-methoxy-3-nitroso-1,5-dihydropyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in methanol was boiled under reflux with 0.25 mol (0.25 mmol) aniline for two minutes. The compound 5-benzylidene-3-nitroso-4-phenylamino-1,5-dihydropyrrol-2-one was obtained in a yield of 30% after recrystallization from methanol. The compound decomposes at 230° C.

Analysis of this compound by means of $^1$H-NMR spectroscopy gave the following signals:
$^1$H-NMR (d6-DMSO, δ in ppm): 10.04 (s, 1H); 7.68–7.11 (m, 10H); 6.10 (s, 1H).

Example 5
5-Benzylidene-4-methylamino-3-nitroso-1,5-dihydropyrrol-2-one

A solution of 0.11 g (0.5 mmol) 5-benzylidene-4-methoxy-3-nitroso-1,5-dihydropyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in methanol was boiled under reflux with 0.25 ml (0.25 mmol) methylamine solution for two minutes. The compound 5-benzylidene-4-methylamino-3-nitroso-1,5-dihydropyrrol-2-one was obtained in a yield of 50% after recrystallization from methanol. The compound decomposes at 220° C.

Analysis of this compound by means of $^1$H-NMR spectroscopy gave the following signals:
$^1$H-NMR (d6-DMSO, δ in ppm): 7.57–7.21 (m, 5H); 6.09 (s, 1H); 3.30 (s, 3H).

Example 6
4-Amino-5-benzylidene-3-nitroso-1,5-dihydropyrrol-2-one

A solution of 0.11 g (0.5 mmol) 5-benzylidene-4-methoxy-3-nitroso-1,5-dihydropyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in methanol was boiled under reflux with 0.25 ml (0.25 mmol) of an aqueous ammonia solution for two minutes. The compound 4-amino-5-benzylidene-3-nitroso-1,5-dihydropyrrol-2-one was obtained in a yield of 45% after recrystallization from methanol. The compound decomposes at 260° C.

Analysis of this compound by means of $^1$H-NMR spectroscopy gave the following signals:
$^1$H-NMR (d6-DMSO, δ in ppm): 10.06 (s, 1H); 7.57–7.23 (m, 5H); 6.08 (s, 1H).

Example 7
5-Benzylidene-4-hydroxy-3-nitro-1,5-dihydropyrrol-2-one 0.5 ml concentrated nitric acid is added to a suspension of 0.18 g (1 mmol) of the corresponding tetramic acid (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)), dissolved in glacial acetic acid. After some minutes a precipitate precipitates out, which is filtered off and washed with a little glacial acetic acid. The yellow crystals of 5-benzylidene-4-hydroxy-3-nitro-1,5-dihydropyrrol-2-one are obtained in a yield of 60% and decompose at 250° C.

Analysis of this compound by means of $^1$H-NMR spectroscopy gave the following signals:
$^1$H-NMR (d6-DMSO, δ in ppm): 11.89 (s, 1H); 7.54–7.18 (m, 5H); 6.14 (s, 1H).

Example 8
5-Benzylidene-3-nitro-4-phenylamino-1,5-dihydropyrrol-2-one

An excess of diazomethane in ether is added to a suspension of 0.46 g (2 mmol) benzylidene-4-hydroxy-3-nitro-3-pyrrol-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in 20 ml methanol. When the evolution of nitrogen has subsided, the solvent is stripped off, the residue is dissolved in methanol and the solution is heated under reflux with an excess of aniline for five minutes, whereupon yellow crystals precipitate out, which are filtered off with suction and washed with methanol. 5-Benzylidene-3-nitro-4-phenylamino-1,5-dihydropyrrol-2-one was obtained in a yield of 50% and decomposes at 236° C.

Analysis of this compound by means of $^1$H-NMR spectroscopy gave the following signals:
$^1$H-NMR (d6-DMSO, δ in ppm): 10.82 (s, 1H); 10.08 (s, 1H); 7.48–7.30 (m, 10H); 6.29 (s, 1H).

Example 9
4-Benzylamino-5-benzylidene-3-nitro-1,5-dihydropyrrol-2-one

An excess of diazomethane in ether is added to a suspension of 0.46 g (2 mmol) benzylidene-4-hydroxy-3-nitro-3-pyrrolin-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in 20 ml methanol. When the evolution of nitrogen has subsided, the solvent is stripped off, the residue is dissolved in methanol and the solution is heated under reflux with an excess of benzylamine for five minutes, whereupon yellow crystals precipitate out, which are filtered off with suction and washed with methanol. 4-Benzylamino-5-benzylidene-3-nitro-1,5-dihydropyrrol-2-one was obtained with a melting point of 218° C. in a yield of 60%.

Analysis of this compound by means of $^1$H-NMR spectroscopy gave the following signals:
$^1$H-NMR (d6-DMSO, δ in ppm): 7.43–7.32 (m, 10H); 6.69 (s, 1H); 5.11 (s, 2H).

Example 10
5-Benzylidene-4-methylamino-3-nitro-1,5-dihydropyrrol-2-one

An excess of diazomethane in ether is added to a suspension of 0.46 g (2 mmol) benzylidene-4-hydroxy-3-nitro-3-pyrrolin-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in 20 ml methanol. When the evolution of nitrogen has subsided, the solvent is stripped off, the residue is dissolved in methanol and the solution is heated under reflux with an excess of methylamine solution for five minutes, whereupon yellow crystals precipitate out, which are filtered off with suction and washed with methanol. 5-Benzylidene-4-methylamino-3-nitro-1,5-dihydropyrrol-2-one was obtained with a melting point of 238° C. in a yield of 45%.

Analysis of this compound by means of $^1$H-NMR spectroscopy gave the following signals:
$^1$H-NMR (d6-DMSO, δ in ppm): 8.85 (s, 1H); 7.42–7.27 (m, 5H); 6.32 (s, 1H); 3.45 (s, 3H).

Example 11
4-Amino-5-benzylidene-3-nitro-1,5-dihydropyrrol-2-one

An excess of diazomethane in ether is added to a suspension of 0.46 g (2 mmol) benzylidene-4-hydroxy-3-nitro-3-pyrrolin-2-one (prepared by the method of H. Poschenrieder et al (Arch. Pharm. Pharm. Med. Chem. 1998, vol. 331, pp. 389–394) and Stachel et al (J. Heterocycl. Chem. 1980, vol. 17, pp. 1195–1199 and Liebigs Ann. Chem. 1985, pp. 1692–1696)) in 20 ml methanol. When the evolution of nitrogen has subsided, the solvent is stripped off, the residue is dissolved in methanol and the solution is heated under reflux with an excess of ammonia solution for five minutes, whereupon yellow crystals precipitate out, which are filtered off with suction and washed with methanol. 4-Amino-5-benzylidene-3-nitro-1,5-dihydropyrrol-2-one obtained with a melting point of >260° C. in a yield of 75%.

Analysis of this compound by means of $^1$H-NMR spectroscopy gave the following signals:
$^1$H-NMR (d6-DMSO, δ in ppm): 9.92 (s, 1H); 9.49 (s, 1H); 9.10 (s, 1H); 7.66–7.34 (m,5H); 7.00 (s, 1H).

Pharmacological studies:

b) Receptor binding studies

The studies for determination of the affinity of the compounds according to the invention according to examples 3 to 6 and 8 to 11 for the glycine-binding site of the NMDA receptor channed was [sic] carried out as described above.

The affinity for the glycine-binding site of the NMDA receptor channel was calculated as the $IC_{50}$ (concentration with 50% displacement of the radioactive ligand from its specific binding) in accordance with the law of mass action be means of non-linear regression and is stated in the following table 1 as the Ki value after conversion (by the Cheng-Prussoff equation (Y. Cheng, W. H. Prusoff, 1973, Biochem. Pharmacol., vol. 22, pp. 3099–3108)).

TABLE 1

| Example | Glycine-binding site of the NMDA receptor channel Ki (μmol/l) |
| --- | --- |
| 3 | 68 |
| 4 | 72 |
| 5 | 60 |
| 6 | 70 |
| 8 | 9 |
| 9 | 5 |
| 10 | 3 |
| 11 | 6 | b) Formalin test in mice

The studies for determination of the antinociceptive action of the compounds according to the invention were carried out as described above.

The corresponding results in the formalin test in mice are summarized in the following table 2.

TABLE 2

| Example | % change with respect to the control at 10 mg/kg |
| --- | --- |
| 1 | 63.9 |
| 2 | 36.3 |
| 3 | 47.6 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. A substituted 1,5-dihydropyrrol-2-one compound of formula I:

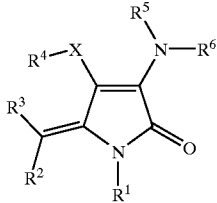

wherein

X represents O or $NR^7$;

$R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, an aryl or a heteroaryl group, or represents an aryl group bonded via a $C_{1-6}$-alkylene group;

$R^2$, $R^3$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-10}$-alkylene group;

$R^4$ represents H, OH, $OR^{11}$, $SR^{11}$, $COR^8$, $COOR^8$, $COCOR^8$, $CONR^9R^{10}$, $CSNR^9R^{10}$, a $C_{1-6}$-alkyl, an aryl or a heteroaryl group, or represents an aryl group bonded via a $C_{1-6}$-alkylene group;

$R^5$, $R^6$, which are identical or different, represent H, O, OH, $OR^{11}$, $SR^{11}$, $CSR^8$, $COOR^8$, $COCOR^8$, $CONR^9R^{10}$, $CSNR^9R^{10}$, a $C_{1-10}$-alkyl, an aryl or a heteroaryl group, or represent an aryl group bonded via a $C_{1-6}$-alkylene group or $R^5$ and $R^6$ together denote the group =O;

$R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;

$R^8$ represents H, $OR^{11}$, $SR^{11}$, $NR^9R^{10}$ a $C_{1-10}$-alkyl, an aryl or a heteroaryl group, or represents an aryl group bonded via a $C_{1-10}$-alkylene group;

$R^9$ represents a $C_{1-10}$-alkyl, an aryl or a heteroaryl group, or represents an aryl group bonded via a $C_{1-6}$-alkylene group;

$R^{10}$ represents a $C_{1-10}$-alkyl, an aryl or heteroaryl group, or represents an aryl group bonded via a $C_{1-6}$-alkylene group; and $R^{11}$ represents a $C_{1-10}$-alkyl, an aryl or a heteroaryl group, or represents an aryl group bonded via a $C_{1-10}$-alkylene group;

in the form of their racemates, enantiomers, diastereomers or a corresponding physiologically tolerated salt.

2. A substituted 1,5-dihydropyrrol-2-one compound according to claim 1, wherein $R^1$ represents a $C_{1-6}$-alkyl group.

3. A substituted 1,5-dihydropyrrol-2-one compound according to claim 1, wherein $R^1$ represents an aryl group bonded via a $C_{1-8}$-alkylene group and the other groups $R^2$ to $R^{11}$ have the meaning according to the general formula I.

4. A substituted 1,5-dihydropyrrol-2-one compound according to claim 1, wherein $R^2$ or $R^8$ represents a $C_{1-6}$-alkyl group.

5. A substituted 1,5-dihydropyrrol-2-one compound according to claim 1, wherein $R^2$ or $R^3$ represents an aryl group bonded via a $C_{1-3}$-alkylene group.

6. A substituted 1,5-dihydropyrrol-2-one compound according to claim 1, wherein $R^4$ represents a $C_{1-6}$-alkyl group.

7. A substituted 1,5-dihydropyrrol-2-one compound according to claim 1, wherein $R^4$ represents an aryl group bonded via a $C_{1-8}$-alkylene group.

8. A substituted 1,5-dihydropyrrol-2-one compound according to claim 1, wherein $R^5$ and $R^6$ together denote the group =O.

9. A substituted 1,5-dihydropyrrol-2-one compound according to claim 1, wherein $R^5$ or $R^6$, or both represent a $C_{1-10}$-alkyl group.

10. A substituted 1,5-dihydropyrrol-2-one compound according to claim 1, wherein $R^5$ or $R^6$ represents an aryl group bonded via a $C_{1-3}$-alkylene group.

11. A substituted 1,5-dihydropyrrol-2-one compound according to claim 1, wherein $R^7$ represents a $C_{1-6}$-alkyl group.

12. A substituted 1,5-dihydropyrrol-2-one compound according to claim 1, wherein $R^7$ represents an aryl group bonded via a $C_{1-6}$-alkylene group.

13. A substituted 1,5-dihydropyrrol-2-one compound according to claim 1, wherein $R^8$ represents a $C_{1-6}$-alkyl group.

14. A substituted 1,5-dihydropyrrol-2-one compounds according to claim 1, wherein $R^5$ represents an aryl group bonded via a $C_{1-6}$-alkylene group.

15. A substituted 1,5-dihydropyrrol-2-one compound according to claim 1, wherein $R^9$ represents a $C_{1-6}$-alkyl group.

16. A substituted 1,5-dihydropyrrol-2-one compound according to claim 1, wherein $R^9$ represents an aryl group bonded via a $C_{1-3}$-alkylene group.

17. A substituted 1,5-dihydropyrrol-2-one compound according to claim 1, wherein $R^{10}$ represents a $C_{1-6}$-alkyl.

18. A substituted 1,5-dihydropyrrol-2-one compound according to claim 1, wherein $R^{10}$ represents an aryl group bonded via a $C_{1-6}$-alkylene group.

19. A substituted 1,5-dihydropyrrol-2-one compound according to claim 1, wherein $R^{11}$ represents a $C_{1-6}$-alkyl group.

20. A substituted 1,5-dihydropyrrol-2-one compound according to claim 1, wherein $R^{11}$ represents an aryl group bonded via a $C_{1-3}$-alkylene group.

21. A substituted 1,5-dihydropyrrol-2-one compound according to claim 1, selected from the group consisting of:

5-benzylidene-4-methoxy-3-nitroso-1,5-dihydropyrrol-2-one;

4-benzylamine-5-benzylidene-3-nitroso-1,5-dihydropyrrol-2-one;

5-benzylidene-4-hydroxy-3-nitroso-1,5-dihydro-pyrrol-2-one;

5-benzylidene-3-nitroso-4-phenylamino-1,5-dihydropyrrol-2-one;

5-benzylidene-4-methylamino-3-nitroso-1,5-dihydropyrrol-2-one;

4-amino-5-benzylidene-3-nitroso-1,5-dihydropyrrol-2-one;

5-benzylidene-4-hydroxy-3-nitro-1,5-dihydropyrrol-2-one;

5-benzylidene-8-nitro-4-phenylamino-1,5-dihydropyrrol-2-one;

4-benzylamino-5-benzylidene-3-nitro-1,5-dihydropyrrol-2-one;

5-benzylidene-4-methylamino-3-nitro-1,5-dihydropyrrol-2-one; and 4-amino-5-benzylidene-3-nitro-1,5-dihydropyrrol-2-one.

22. A method for the preparation of a substituted 1,5-dihydropyrrol-2-one compound of formula I:

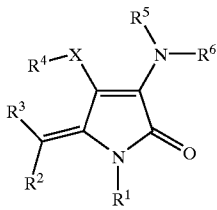

wherein
X represents O or $NR^7$;
$R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl an aryl or a heteroaryl group, or represents an aryl group bonded via a $C_{1-6}$-alkylene group;
$R^2$, $R^3$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-6}$-alkylene group;
$R^4$ represents H, OH, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^5$, $R^6$, which are identical or different, represent H, O, OH, $OR^{11}$, $SR^{11}$, $CSR^8$, $COOR^8$, $COCOR^8$, $CONR^9R^{10}$, $CSNR^9R^{10}$, a $C_{1-10}$-alkyl, an aryl or a heteroaryl group, or represent an aryl group bonded via a $C_{1-6}$-alkylene group or $R^5$ and $R^6$ together denote the group =O;
$R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^8$ represents H, $OR^{11}$, $SR^{11}$, $NR^9R^{10}$, a $C_{1-10}$-alkyl, an aryl or a heteroaryl group, or represents an aryl group bonded via a $C_{1-10}$-alkylene group;
$R^9$ represents a $C_{1-10}$-alkyl, an aryl or a heteroaryl group, or represents an aryl group bonded via a $C_{1-6}$-alkylene group; represents a $C_{1-10}$-alkyl, an aryl or a heteroaryl group, or represents an aryl group bonded via a $C_{1-6}$-alkylene group; and
$R^{11}$ represents a $C_{1-10}$-alkyl, an aryl or a heteroaryl group, or represents an aryl group bonded via a $C_{1-6}$-alkylene group,
the method comprising
A. reacting a tetram acid of formula II:

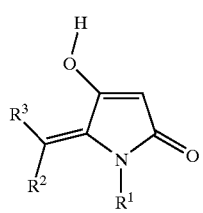

wherein $R^1$ to $R^8$ have the meanings according to formula I, with an aqueous solution of an alkali metal nitrite at a low temperature in solution, to give rise to a compound of formula III:

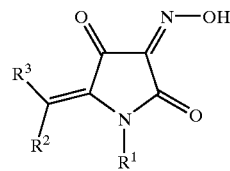

wherein $R^1$ to $R^2$ have the meanings according to formula I;
B. converting a compound of formula III by alkylation with an alkylating agent or by reaction with an acid chloride, acid bromide, chlorocarbonic acid ester, fluorocarbonic acid ester, isocyanate or isothiocyanate in a non-polar solvent or a polar, aprotic solvent, or a polar, protic solvent into a compound of formula IV:

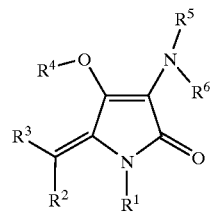

wherein $R^1$ to $R^4$ have the meanings according to formula I, and $R^5$ and $R^6$ together denote the group =O;
C. optionally derivatizing a compound of formula IV, wherein $R^1$ to $R^4$ have the meanings according to formula II, and $R^5$ and $R^8$ together denote the group =O, by reaction with a nucleophilte in a polar solvent to give a compound of formula V:

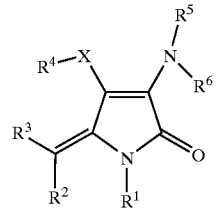

wherein $R^1$ to $R^4$ and X have the meanings according to formula I, and $R^5$ and $R^6$ together denote the group =O;
D. optionally reducing a compound of formula V, wherein $R^1$ to $R^4$ and X have the meanings according to formula I, and $R^5$ and $R^6$ together denote the group =O, to a compound of formula I, wherein $R^1$ to $R^4$ and X have the meanings according to formula I, and $R^5$ and $R^6$ each denote H by reaction with a reducing agent; and
E. optionally further derivatizing a compound of formula V, wherein wherein $R^1$ to $R^4$ and X have the meanings according to formula I, and $R^5$ and $R^6$ each denote H, to give a compound of formula I, wherein $R^1$ to $R^4$ and X have the meanings according to formula I, and $R^6$ and $R^8$ are identical or different and each represent O, OH, $OR^{11}$, $SR^{11}$, $CSR^9$, $COOR^8$, $COCOR^8$, $CONR^9R^{10}$, $CSNR^9R^{10}$, a $C_{1-10}$-alkyl group, an aryl group or a heteroaryl group, or represent an aryl group bonded via a $C_{1-6}$-alkylene group.

23. A method according to claim 22 for the preparation of a substituted 1,5-dihydropyrrol-2-one compound of formula I;

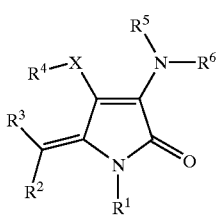

wherein
X represents O or $NR^7$; $R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, an aryl or a heteroaryl group, or represents an aryl group bonded via a $C_{1-6}$-alkylene group;
$R^2$, $R^3$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-6}$-alkylene group;
$R^4$ represents H, OH, $OR^{11}$, $SR^{11}$, $COR^8$, $COOR^8$, $COCOR^8$, $CONR^9R^{10}$, $CSNR^9R^{10}$, a $C_{1-6}$-alkyl, an aryl or a heteroaryl group, or represents an aryl group bonded via a $C_{1-6}$-alkylene group;
$R^5$, $R^6$, which are identical or different, represent H, O, OH, $OR^{11}$, $SR^{11}$, $COR^8$, $COOR^8$, $COCOR^8$ $CONR^9R^{10}$, $CSNR^9R^{10}$, a $C_{1-10}$-alkyl, an aryl or a heteroaryl group, or represent an aryl group bonded via a $C_{1-6}$-alkylene group or $R^5$ and $R^6$ together denote the group =O;
$R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^8$ represents H, $OR^{11}$, $SR^{11}$ $NR^9R^{10}$, a $C_{1-10}$-alkyl, an aryl or a heteroaryl group, or represents an aryl group bonded via a $C_{1-6}$-alkylene group;
$R^9$ represents a $C_{1-10}$-alkyl, an aryl or a heteroaryl group, or represents an aryl group bonded via a $C_{1-6}$-alkylene group;
$R^{10}$ represents a $C_{1-10}$-alkyl, an aryl or a heteroaryl group, or represents an aryl group bonded via a $C_{1-6}$-alkylene group; and
$R^{11}$ represents a $C_{1-10}$-alkyl, an aryl or a heteroaryl group, or represents an aryl group bonded via a $C_{1-6}$-alkylene group,
wherein the method comprises
A. reacting a tetram acid of the formula II:

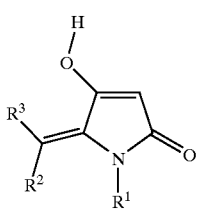

wherein $R^1$ to $R^8$ have the meanings according to formula I, with an aqueous solution of an alkali metal nitrite at a low temperature in solution, to give rise to a compound of the general formula III:

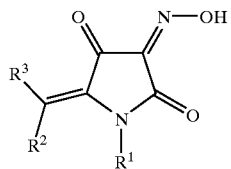

wherein $R^1$ to $R^3$ have the meaning meanings according to the general formula and B. converting a compound of formula III by alkylation with an alkylating agent or by reaction with an acid chloride, acid bromide, chlorocarbonic acid ester, fluorocarbonic acid ester, isocyanate or isothiocyanate in a non-polar solvent or a polar, aprotic solvent, or a polar, protic solvent into a compound of formula IV:

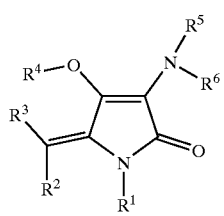

wherein $R^1$ to $R^4$ have the meanings according to the general formula I and $R^5$ and $R^6$ together denote the group =O.

24. The method according to claim 23, wherein the alkali metal nitrite is sodium nitrite.

25. The method according to claim 23, wherein the solution is an ice-cooled acid solution.

26. The method according to claim 25, wherein the ice-cooled acid solution is glacial acetic acid solution.

27. The method according to claim 23, wherein the compound of formula III in step A is purified.

28. The method according to claim 27, wherein the compound of formula III in step A is purified via recrystallization.

29. The method according to claim 28, wherein the compound of formula III in step A is purified via recrystallization from ethanol.

30. A method according to claim 23, where the alkylating agent is selected from the group consisting of diazoalkanes, dialkyl sulfates, and alkyl halides, and a mixture of two thereof.

31. The method according to claim 28, wherein the alkylating agent is diazoalkanes in ethereal solution.

32. A method according to claim 23, wherein the nonpolar solvent is an open-chain or cyclic ether, a hydrocarbon, or a halogen-containing hydrocarbon.

33. The method according to claim 23, further comprising purifying the compound of Formula IV.

34. A method according to claim 22, for the preparation of a substituted 1,5-dihydropyrrol-2-one compound of formula I;

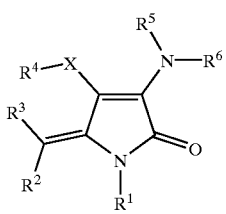

wherein
X represents O or $NR^7$;
$R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, an aryl or a heteroaryl group, or represents an aryl group bonded via a $C_{1-6}$-alkylene group;
$R^2$, $R^3$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-6}$-alkylene group;
$R^4$ represents H, OH, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^5$ and $R^6$ together denote the group =O;
$R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^8$ represents H, $OR^{11}$, $SR^{11}$, $NR^9R^{10}$ a $C_{1-10}$-alkyl, an aryl or a heteroaryl group, or represents an aryl group bonded via a $C_{1-6}$-alkylene group;
$R^9$ represents a $C_{1-10}$-alkyl, an aryl or a heteroaryl group, or represents an aryl group bonded via a $C_{1-6}$-alkylene group;
$R^{10}$ represents a $C_{1-10}$-alkyl, an aryl or a heteroaryl group, or represents an aryl group bonded via a $C_{1-10}$-alkylene group; and
$R^{11}$ represents a $C_{1-10}$-alkyl, an aryl or a heteroaryl group, or represents an aryl group bonded via a $C_{1-6}$-alkylene groups
wherein the method comprises reacting a compound of formula IV:

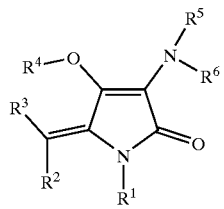

wherein $R^1$ to $R^4$ have the meaning meanings according to formula I and $R^5$ and $R^6$ together deonute the group =O, with a nucleophile in a polar solvent.

35. The method according to claim 34, further comprising purifying the compounds of Formula I wherein $R^5$ and $R^6$ together denote =O.

36. The method according to claim 35, wherein the recrystalization is from methanol, ethanol, isopropanol, or a mixture thereof.

37. A method according to claim 34, wherein the nucleophile is a primary or secondary amine, aliphatic, aromatic or heteroaromatic alcoholate, or phenolate.

38. A method according to claim 34, wherein the polar solvent is methanol, ethanol or isopropanol.

39. A method according to claim 22 for the preparation of a substituted 1,5-dihydropyrrol-2-one compound of formula I:

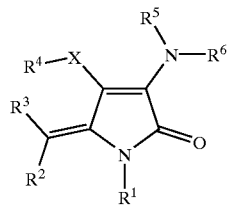

wherein
X represents O or $NR^7$;
$R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, an aryl or a heteroaryl group, or represents an aryl group bonded via a $C_{1-6}$-alkylene group;
$R^2$, $R^8$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-6}$-alkylene group;
$R^4$ represents H, OH, $OR^{11}$, $SR^{11}$, $COR^8$, COORS, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^5$ and $R^6$ each denotes H;
$R^7$ represents H, $OR^{11}$, $SR^{11}$, $COR^8$, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;
$R^8$ represents H, $OR^{11}$, $SR^{11}$, $NR^9R^{10}$, a $C_{1-10}$-alkyl, an aryl or a heteroaryl group, or represents an aryl group bonded via a $C_{1-6}$-alkylene group;
$R^9$ represents a $C_{1-10}$-alkyl, an aryl or a heteroaryl group, or represents an aryl group bonded via a $C_{1-6}$-alkylene group;
$R^{10}$ represents a $C_{1-10}$-alkyl, an aryl or a heteroaryl group, or represents an aryl group bonded via a $C_{1-6}$-alkylene group; and
$R^{11}$ represents a $C_{1-10}$-alkyl, an aryl or a heteroaryl group, or represents an aryl group bonded via a $C_{1-6}$-alkylene group;
wherein the method comprises reducing a compound of the formula I wherein $R^5$ and $R^6$ together denote =O.

40. The method according to claim 39 further comprising purifying the compound of formula I wherein $R^5$ and $R^6$ eat denotes H.

41. A method according to claim 39 wherein the compound of formula I wherein $R^5$ and $R^6$ together denote =O is reduced with Zn/glacial acetic acid, lithium aluminium hydride, $BH_3$, $Na[BH_3CN]/TiCl_3$, sodium alkoxides or hydrogen in the presence of a transition metal catalyst.

42. A pharmaceutical composition comprising a substituted 1,5-dihydropyrrol-2-one compound of formula Ia:

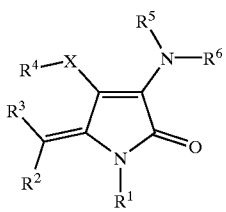

wherein

X represents O, S or $NR^7$;

$R^1$ represents H, $OR^{11}$, $SR^{11}$, $COR^8$, $CSR^8$, $NR^9R^{10}$, $COOR^8$, $CONR^9R^{10}$, $CSNR^9R^{10}$, $COCOR^8$, a $C_{1-10}$-alkyl, an aryl or a heteroaryl group, or represents an aryl group bonded via a $C_{1-6}$-alkylene group;

$R^2$, $R^3$, which are identical or different, represent H, F, Cl, Br, $CF_3$, $OR^{11}$, $SR^{11}$, $NR^9R^{10}$, a $C_{1-10}$-alkyl, an aryl or a heteroaryl group, or represent an aryl group bonded via a $C_{1-6}$-alkylene group;

$R^4$ represents H, OH, $OR^{11}$, $SR^{11}$, CORE, $COOR^8$, $COCOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;

$R^5$, $R^6$, which are identical or different, represent H, O, OH, $OR^{11}$, $SR^{11}$, $CSR^8$, $COOR^8$, $COCOR^8$, $CONR^9R^{10}$, $CSNR^9R^{10}$, a $C_{1-10}$-alkyl, an aryl or a heteroaryl group, or represent an aryl group bonded via a $C_{1-6}$-alkylene group or $R^5$ and $R^6$ together denote the group =O;

$R^7$ represents H, $OR^{11}$, $SR^{11}$, $COR^8$, $COOR^8$, $COOR^8$, $CONR^9R^{10}$, $CSNR^9R^{10}$, a $C_{1-10}$-alkyl, an aryl or a heteroaryl group, or represents an aryl group bonded via a $C_{1-6}$-alkylene group;

$R^8$ represents H, $OR^{11}$, $SR^{11}$, $NR^9R^{10}$, a $C_{1-10}$-alkyl, an aryl or a heteroaryl group, or represents an aryl group bonded via a $C_{1-6}$-alkylene group;

$R^9$ represents a $C_{1-10}$-alkyl, an aryl or a heteroaryl group, or represents an aryl group bonded via a $C_{1-6}$-alkylene group;

$R^{10}$ represents a $C_{1-10}$-alkyl, an aryl or a heteroaryl group, or represents an aryl group bonded via a $C_{1-6}$-alkylene group;

$R^{11}$ represents a $C_{1-10}$-alkyl, an aryl or a heteroaryl group, or represents an aryl group bonded via a $C_{1-6}$-alkylene group;

in the form of its racemate, its enantiomers, its diastereomers or a corresponding physiologically tolerated salt, and a pharmaceutically acceptable excipient.

43. A method for the treatment of pain, inflammatory and allergic reactions, depressions, drug and/or alcohol abuse, gastritis, diarrhoea, urinary incontinence, cardiovascular diseases, respiratory tract diseases, coughing, mental illnesses or epilepsy, schizophrenia, Alzheimer's diseases, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome, perinatal asphyxia, tinnitus aurium or anxiolysis, the method comprising administering an effective amount of a pharmaceutical composition of claim 42 to a patient in need thereof.

44. A method according to claim 43 wherein the method is for the treatment of pain, inflammatory and allergic reactions, depressions, drug and/or alcohol abuse, gastritis, diarrhoea, urinary incontinence, cardiovascular diseases, respiratory tract diseases, coughing, mental illnesses or epilepsy.

45. A method according to claim 43, wherein the method is for the treatment of schizophrenia, Alzheimer's diseases, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome, perinatal asphyxia, tinnitus aurium or for anxiolysis.

* * * * *